United States Patent [19]

Ranoux

[11] Patent Number: 5,135,865
[45] Date of Patent: Aug. 4, 1992

[54] CONTAINER FOR FERTILIZATION OF HUMAN OVOCYTES IN THE ABSENCE OF $CO_2$-ENRICHED AIR

[76] Inventor: Claude Ranoux, 7 Rue des Grands Champs, 77330 Lesigny, France

[21] Appl. No.: 329,640

[22] Filed: Mar. 28, 1989

Related U.S. Application Data

[62] Division of Ser. No. 80,537, Jul. 6, 1987, Pat. No. 4,902,286.

[30] Foreign Application Priority Data

Nov. 8, 1985 [FR] France .................................. 85-16558

[51] Int. Cl.⁵ .......................... C12N 5/00; A61B 17/00; A61M 31/00; A61D 19/00
[52] U.S. Cl. .............................. 435/240.2; 435/240.21
[58] Field of Search .................. 435/240.4; 600/33, 34, 600/35; 604/55, 906

[56] References Cited

U.S. PATENT DOCUMENTS

| | | |
|---|---|---|
| 1,877,766 | 9/1932 | Kennedy . |
| 2,456,607 | 12/1948 | Shaffer . |
| 2,707,471 | 5/1955 | Koff . |
| 2,818,064 | 12/1957 | Leff . |
| 3,239,429 | 3/1966 | Menolasino et al. . |
| 3,805,784 | 4/1974 | Alter . |
| 3,875,012 | 4/1975 | Dorn et al. . |
| 4,300,544 | 11/1981 | Rudel . |
| 4,380,997 | 4/1983 | Leibo .................. 128/1 R |
| 4,380,997 | 4/1983 | Leibo . |
| 4,427,477 | 1/1984 | Milgrom . |
| 4,533,345 | 8/1985 | Louw . |
| 4,555,037 | 11/1985 | Rhees . |
| 4,579,823 | 4/1986 | Ryder . |
| 4,589,402 | 5/1986 | Hodgen et al. ............. 128/1 R |
| 4,598,045 | 7/1986 | Masover et al. . |
| 4,725,579 | 2/1988 | Jones et al. ............. 514/12 |
| 4,747,500 | 5/1988 | Gach et al. . |
| 4,761,379 | 8/1988 | Williams et al. . |

FOREIGN PATENT DOCUMENTS

| | | |
|---|---|---|
| 114799 | 3/1942 | Australia . |
| 149242 | 8/1949 | Australia . |
| 23591/77 | 3/1977 | Australia . |
| 58425/80 | 11/1980 | Australia . |
| 18159/83 | 2/1984 | Australia . |
| 19729/83 | 9/1984 | Australia . |
| 0131166 | 1/1985 | European Pat. Off. . |
| 2194453 | 3/1974 | France . |
| 0558998 | 1/1944 | United Kingdom . |
| 43002 | 2/1970 | United Kingdom . |
| 2158093 | 11/1985 | United Kingdom . |

OTHER PUBLICATIONS

"A New in Vitro Fertilization Technique: Intravaginal Culture", *Fertility and Sterility*, vol. 49, No. 4, Apr. 1988, by C. Ranoux et al., pp. 654 et seq.

Primary Examiner—David L. Lacey
Assistant Examiner—Gian P. Wang
Attorney, Agent, or Firm—Young & Thompson

[57] ABSTRACT

The invention relates to a container for fertilization of human ovocytes in the absence of $CO_2$ which may be done in an incubator at 37° C. or in the vaginal cavity. The container will be held in the posterior fornix of the vaginal cavity by a flexible ring comprised of a metal strip 17 sheathed in rubber 18 to which is fixed a rubber pouch 19 in which the container is placed. This device thus permits inter-vaginal fertilization of human ovocytes in the absence of $Cl_2$-enriched air, the vaginal cavity replacing the incubator conventionally used.

24 Claims, 2 Drawing Sheets

CONTAINER FOR FERTILIZATION OF HUMAN OVOCYTES IN THE ABSENCE OF $CO_2$-ENRICHED AIR

This application is a division of application Ser. No. 07/080,537, filed Jul. 6, 1987, now U.S. Pat. No. 4,902,286.

This invention concerns a totally new procedure for fertilizing human ovocytes, making use of a device that we will describe.

In vitro fertilization of human ova is a very complex technique which permits a solution for cases of infertility of couples which up to then were irreversible. Since the first birth, of Louise Brown, in 1978, achieved by the Edwards team in England, thousands of children have been born worldwide through this technique.

The major concern of all teams working in vitro fertilization has always been to obtain a simplification of the technique while maintaining or improving the results. Thus from the clinical standpoint there has appeared:

stimulation to obtain a plurality of ovocytes thereby increasing the chances of success, methods of ovarian puncture other than under coelioscopic control, namely under transvesical, then transvaginal and finally transurethral ultrasonic control which enabled general anesthesia to be eliminated and possible $CO_2$ toxicity to be avoided. From the biological standpoint the freezing of supernumerary embryos has permitted an improvement of results. Only the biological stage of fertilization per se has undergone but minimal changes.

It has remained very complex to date. Conventionally it involved aerobic or sterile culturing of embryos in a box or tube at 37° C. and under a 5% $CO_2$ atmosphere. This requires non-hermetically sealed boxes or tubes with a risk of contamination by the surroundings. Hence the need for a $CO_2$ incubator (developed by "Testart") perfectly controlled at 37° C. and in $CO_2$. This equipment is cumbersome and expensive.

Similarly, initially, after puncture, one proceeded to a 1-to-4 hour maturation phase of the ovocytes in a culture medium usually enriched with human serum and, after this period, the fertilization of the ovocytes, changing the medium 18 to 24 hours after the stripping of the ova was effected. (This stripping involves the mechanical removal of the cumulus surrounding the ovum to observe the stage of development.) The ovum was then transferred to a new medium which after 20 to 24 hours was again changed before transfer into the uterine cavity, which involved the use of more than 3 ml of culture medium per ovum and numerous manipulations spread over 48 hours, which could be toxic to the ova.

The procedure that we have developed and whose scientific steps we will summarize is characterized by its simplicity and savings in time and money.

This procedure comprises fertilization of human ovocytes in the absence of $CO_2$-enriched air with the help of a fluidtight tube completely filled with culture medium that is placed in the vagina cavity which then serves as an incubator. Upon puncture of the ovocytes which was delayed (so as to avoid the ovocyte maturation phase), they are placed in the container along with the spermatozoa necessary for fertilization which were previously prepared. Then the device with its holding means is placed in the vaginal cavity from where it will be removed 44 to 48 hours later in order to reintroduce the ova in the uterine cavity by means of a "Frydman" catheter.

The invention will be better understood by consideration of the following description, taken in connection with the accompanying drawings, in which.

Figure 1:
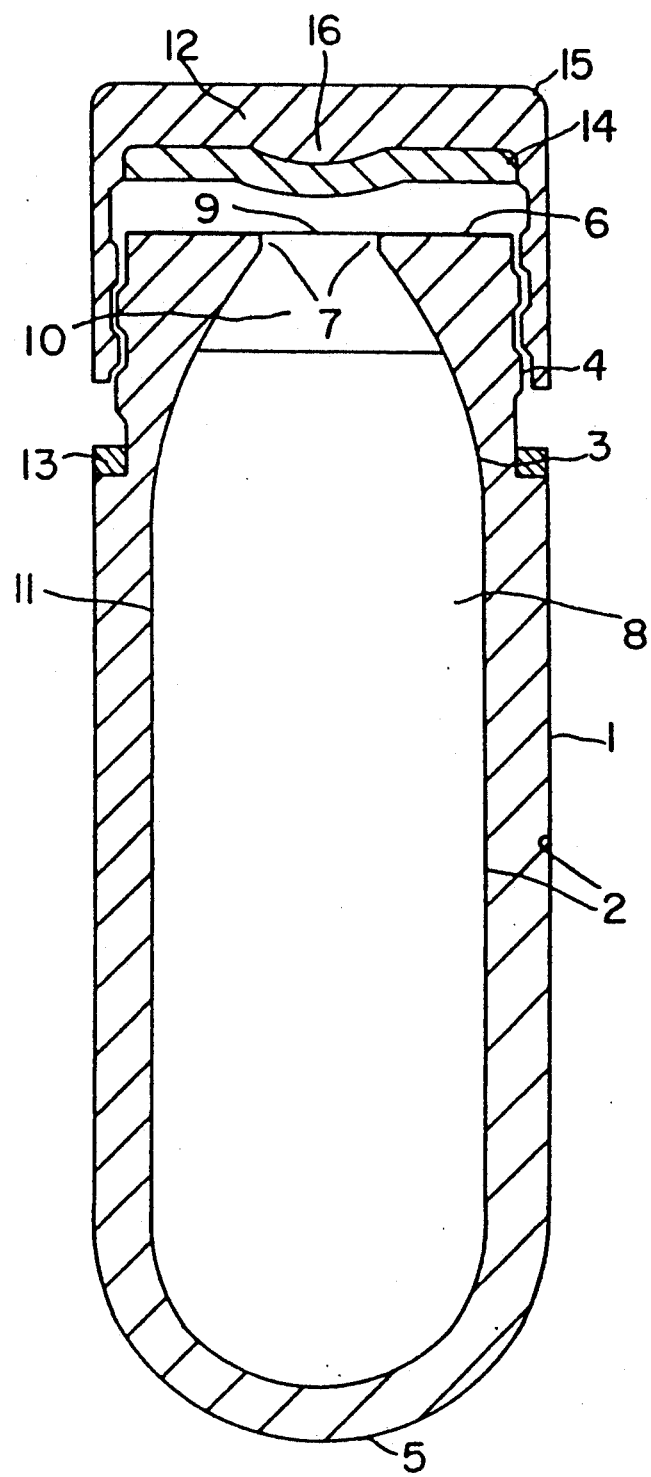
FIG. 1 is a cross sectional view of a container according to the present invention.

We are going to describe an embodiment of the container which constitutes the device (FIG. 1). smooth and rounded outer walls (1) in order to avoid any trauma to the vaginal mucosa. Its approximate dimensions are 4 cm long and 1.5 cm outer diameter; the thickness of the walls is 2 mm for the body (2) of the cylinder except in the region of the neck (3) where it is not more than only 1 mm, which gives an inner cavity of 1.1 cm in diameter and 3.8 cm long with an effective volume of about 3.2 cm$^3$. This volume is suitable for culture of 4 to 5 embryos. For a number of embryos greater than five, the volume of medium used may be increased to 5 cm$^3$, the outer dimensions will then be 4.5 cm long and 1.7 cm outer diameter, the thickness of the wall remaining the same. Likewise shapes other than the cylindrical shape can be envisaged: round, archlike or pear-shaped depending on the configuration of the vagina.

On the outer wall of the body of the tube a marking surface must be provided for the patient's name. On the outer wall of the plug a screw limits aseptic defects.

Due to the decrease in the thickness of the wall of the neck, the outer edge of the plug, once it is screwed on, does not protrude beyond the wall of the tube.

The blind end (5) of the tube is rounded.

The upper end (6) of the tube adjacent the neck is flat and has at its center a round orifice (7) of about 4 mm in diameter. The ovocytes and the spermatozoa necessary for fertilization will be deposited through this orifice. The dimensions of the orifice has been purposely reduced in relation to the diameter of the tube in order to limit the communication between the culture medium and the surrounding atmosphere and therefore to minimize disorders caused thereby.

To reduce further septic risks, the medium disorders and the length of handling time, it seemed advisable to us to devise containers in which the culture (8) medium is placed in the tube at the time of its manufacture.

To avoid biochemical disorders to the medium between the time of manufacture and use, a hermetic closure of the tube will be effected by a thin membrane (9) covering the orifice. This membrane will be made so as to rupture easily when the ovocytes (22) and spermatozoa (24) are deposited in the tube by means of a glass "Pasteur pipette" (21, 23) or a throwaway plastic pipette end piece. Other types of sealed closure may be used such as a device with a valve.

The culture medium may be one of those conventionally used and marketed. The one that we use is the "I.N.R.A. de Menezo" medium marketed under the name "B2" by "A.P.I. Systeme". There will remain only a small volume (10) of gas of about 200 µl between the surface of the medium and the membrane, corresponding to the volume of the ovocytes and spermatozoa transferred.

The inner walls (11) of the tubes must be perfectly smooth and rounded to avoid one of the ova remaining attached when they are removed and transferred to the uterine cavity.

The plug (12) of about 1 cm in height by 1.5 cm in diameter will be screwed onto the neck of the tube to close off the orifice. After rupturing the membrane, perfect fluidtightness is, however, necessary to avoid medium disorders and possible contamination resulting from it being placed in the vaginal cavity. This fluidtightness will be ensured by two seals, one (13) annular, gripping the neck of the tube, about 1 mm thick, the other (14) flat and round overlying the end wall of the plug, of identical thickness. To perfect fluidtightness, the underside of the plug has a relief portion (16) whose diameter is substantially equal to that of the orifice and which enables, when the plug is screwed on, the seal to be applied against the mouth of the orifice of the tube.

The outer wall of the plug has rounded edges (15).

The manufacturing material used will be a rigid plastic having a high mechanical strength (in case of trauma), of the polypropylene type, and non-toxic to cell cultures.

Figure 2A:
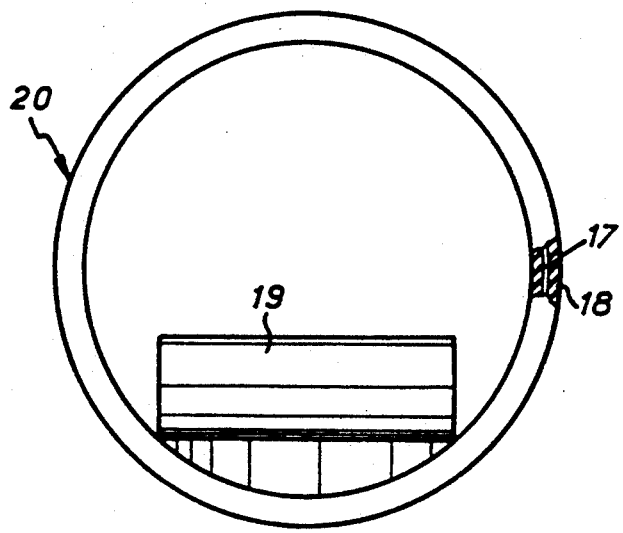
FIG. 2A is an elevational view of a pouch and ring for maintaining the container of FIG. 1 in place.
Figure 2B:
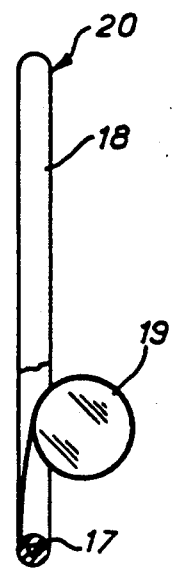
FIG. 2B is an edgewise view, partly broken away, of the structure showing in FIG. 2A.

The tube and the sterile medium will be individually packed in a sterile package of the cellophane paper type; at the time of packing the plug will not be completely tightened in order to avoid rupturing the membrane. A holding device (20) for maintaining the tube in the vaginal cavity is illustrated in FIGS. 2A and 2B. This device (20) comprises a flexible ring made of a metal strip (17) sheathed in rubber (18) to which is attached a small rubber pouch (19) the size of the tube and permits the tube to be slid therein. The diameter of the ring will be determined, like a diaphragm, for each patient individually as a function of the size of the uterine cavity and cervix at a consultation prior to in vitro fertilization. This device enables the holding of the tube in the posterior fornix of the vagina without risk of loss, or cooling of the culture medium due to a position too close to the vaginal introitus.

Figure 1A:
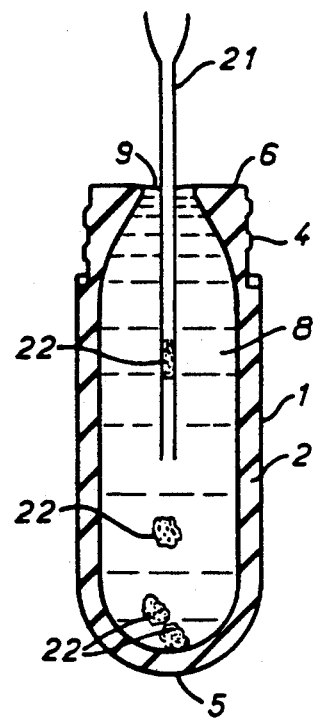
FIG. 1A and 1B are schematic views showing the methods of using the container of FIG. 1.
Figure 1B:
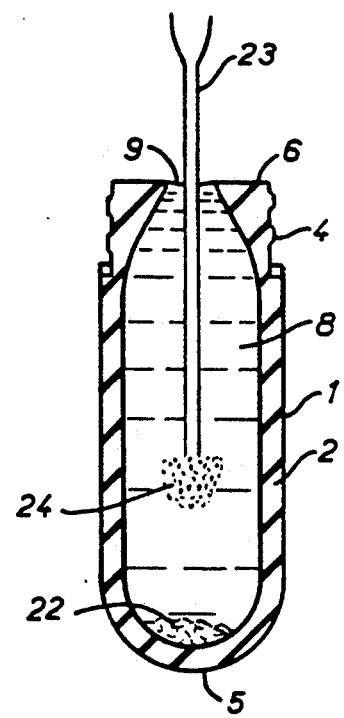

FIGS. 1A and 1B illustrate the insertion of pipettes (21, 23) through the membrane (9) to introduce ovocytes (22) and spermatozoa (24) respectively.

The approach which enabled us to develop this technical procedure and the device is based on findings and work research. The first such finding observed over six months was that a fraction of culture medium kept in a sterile, hermetically sealed (air-free to the extent possible) enabled it to be preserved for more than 10 days without disorders, and without its use changing the results conventionally obtained. The second finding is based on fertilization studies of three ovocytes placed in the same box well, that is, with 1 µl of medium; it demonstrates a cleavage rate identical to that obtained conventionally when a single ovocyte is cultivated per well. Also, the fact that if an ovum is left 48 hours in the same medium necessary for fertilization, this does not interfere with its stage of development.

Finally, a multiplicity of studies including those carried out with "Menezo" showed very minor changes in the culture medium before and after fertilization.

The sum of these findings prompted us to do preliminary studies which, despite the small number of patients, ovocytes and ova involved, induced us to go forward, since the initial results were very encouraging.

A first study on eight patients who had more than four ovocytes per puncture was carried out. About half of the ova obtained were cultured conventionally, the other half were cultured in the hermetically sealed tube and incubated 48 hours. No difference in the cleavage rate was observed. Two patients became pregnant, which corresponds to the success rate conventionally obtained.

In a second group of eight patients also having more than four ovocytes per puncture, about half were conventionally cultured and the other half were placed inside the vagina in a tube containing ova. Here again, the cleavage percentage was substantially the same and even slightly better with the intra-vaginal technique. Five of these patients became pregnant.

Even though the groups are too small to perform statistical analysis and therefore it is too early to draw conclusions, these results are very encouraging and while continuing a comparative study of the conventional culture method with the intra-vaginal technique, we have started pure intra-vaginal cultures; with the first two attempts, one of them resulted in the start of a pregnancy.

The advantages are great and numerous: savings in time and manipulations thus reducing the septic risks and toxicity to ova. Substantial financial savings by reasons of a lesser quantity of medium and simple lab equipment. And most of all, by eliminating the necessity of an expensive $CO_2$ incubator. The operational simplicity enables a lab technicians to be quickly trained, and therefore widespread disemination of the technique. A fundamental psychological contribution is the patient feeling more directly involved in the fertilization of her ova. It is perhaps too soon to envisage, but the good early results obtained are possibly related to culturing being carried out at a temperature which varies in full periods of one day and one night which no incubator is able to reproduce at present. This thermal variation may, totally hypothetically, be playing an important role in the development of the ovum. This procedure also permits the transportation of the ovocytes and the embryons by the patient herself or in a receptacle specially designed for a stabilized temperature of 37° C.

I claim:

1. A process for in vitro fertilization and culture of ovocytes comprising the steps of: introducing into a container an appropriate quantity of a culture medium suitable for fertilization and culture of ovocytes, as well as ovocytes and spermatozoa, hermetically sealing the container, and incubating the contents of the container at a temperature and for a period of time for fertilization and culture of the ovocytes, the steps of hermetically sealing the container and incubating the contents of the container being carried out in the absence of a $CO_2$-enriched atmosphere.

2. A process according to claim 1, wherein the incubation is carried out in a receptacle maintained at a temperature of about 37° C.

3. A process according to claim 1, wherein the incubation is carried out in a mammalian vagina.

4. A process according to claim 1, wherein the ovocytes and spermatozoa are human and the incubation step is carried out in a human vagina and the container is suitably configured for accommodation in the human vagina.

5. A process according to claim 1, wherein the container is initially substantially filled with the culture medium, and initially hermetically sealed before introducing the ovocytes and spermatozoa.

6. A process according to claim 5, wherein the initial hermetic seal is broken in order to introduce ovocytes and spermatozoa, and the container is resealed after the introduction of ovocytes and spermatozoa.

7. A process according to claim 4, wherein the container resides in the human vagina for a period of 44 to 48 hours.

8. A process according to claim 4, wherein the container is placed in the vagina at a location spaced from the vaginal introitus to avoid cooling.

9. A process according to claim 8, wherein the container is located in the posterior fornix.

10. A process according to claim 9, wherein the container is placed in a holder located in the posterior fornix.

11. A process according to claim 5, wherein culture medium is initially hermetically sealed so that it is substantially air free.

12. A process according to claim 5, wherein a head space of about 200 μl is left between the culture medium and the container.

13. A process according to claim 4, wherein the ovocytes and spermatozoa are introduced by means of pipettes.

14. A process for in vitro fertilization and culture of ovocytes comprising the steps of: providing a container suitably configured for accommodation in a mammalian vagina, introducing into the container an appropriate quantity of a culture medium suitable for fertilization and culture of ovocytes, as well as ovocytes and spermatozoa, hermetically sealing the container, and placing the container in a mammalian vagina for a period of time sufficient for fertilization and culture of the ovocytes.

15. A process according to claim 14, wherein the ovocytes and spermatozoa are human and the incubation step is carried out in a human vagina and the container is suitably configured for accommodation in the human vagina.

16. A process according to claim 14, wherein the container is initially substantially filled with the culture medium, and initially hermetically sealed before introducing the ovocytes and spermatozoa.

17. A process according to claim 16, wherein the initial hermetic seal is broken in order to introduce ovocytes and spermatozoa, and the container is sealed after the introduction of ovocytes and spermatozoa.

18. A process according to claim 15, wherein the container resides in the human vagina for a period of 44 to 48 hours.

19. A process according to claim 14, wherein the container is placed in the vagina at a location spaced from the vaginal introitus to avoid cooling.

20. A process according to claim 14, wherein the container is located in the posterior fornix.

21. A process according to claim 20, wherein the container is placed in a holder located in the posterior fornix.

22. A process according to claim 14, wherein culture medium is initially hermetically sealed so that it is substantially air free.

23. A process according to claim 14, wherein a head space of about 200 μl is left between the culture medium and the container.

24. A process according to claim 14, wherein the ovocytes and spermatozoa are introduced by means of pipettes.

* * * * *